United States Patent
Anderson et al.

(10) Patent No.: US 7,623,990 B2
(45) Date of Patent: Nov. 24, 2009

(54) SYSTEM FOR REDUCING SIGNAL INTERFERENCE IN MODULATED SIGNAL COMMUNICATION

(75) Inventors: Ralph Anderson, Lexington, MA (US); Michael Bernstein, San Ramon, CA (US)

(73) Assignee: Draeger Medical Systems, Inc., Andover, MA (US)

(*) Notice: Subject to any disclaimer, the term of this patent is extended or adjusted under 35 U.S.C. 154(b) by 704 days.

(21) Appl. No.: 11/266,001

(22) Filed: Nov. 3, 2005

(65) Prior Publication Data

US 2006/0092328 A1    May 4, 2006

Related U.S. Application Data

(60) Provisional application No. 60/624,670, filed on Nov. 3, 2004.

(51) Int. Cl.
*H03F 1/26* (2006.01)
*H04B 15/00* (2006.01)

(52) U.S. Cl. ............ 702/191; 702/189; 455/63.1; 455/67.11; 329/349; 329/351; 329/353

(58) Field of Classification Search ............... 600/332, 600/333; 375/346
See application file for complete search history.

(56) References Cited

U.S. PATENT DOCUMENTS

| | | | |
|---|---|---|---|
| 4,653,498 A | 3/1987 | New, Jr. et al. | |
| 4,800,885 A * | 1/1989 | Johnson | 600/330 |
| 4,843,339 A * | 6/1989 | Burt et al. | 330/10 |
| 4,869,254 A | 9/1989 | Stone et al. | |
| 5,503,148 A | 4/1996 | Pologe et al. | |
| 5,713,355 A * | 2/1998 | Richardson et al. | 600/336 |
| 5,846,190 A | 12/1998 | Woehrle | |
| 5,885,213 A * | 3/1999 | Richardson et al. | 600/336 |
| 6,370,408 B1 * | 4/2002 | Merchant et al. | 600/322 |
| 6,778,923 B2 * | 8/2004 | Norris et al. | 702/74 |
| 7,142,818 B2 * | 11/2006 | Hunter et al. | 455/63.1 |

FOREIGN PATENT DOCUMENTS

| | | |
|---|---|---|
| EP | 0 502 717 A1 | 9/1992 |
| EP | 1 453 211 A2 | 9/2004 |

* cited by examiner

*Primary Examiner*—Hal D Wachsman
*Assistant Examiner*—Ronald L Biegel
(74) *Attorney, Agent, or Firm*—Jack Schwartz & Associates, PLLC

(57) ABSTRACT

A system for reducing signal interference in modulated signal communication includes a measurement processor. The measurement processor measures amplitudes of noise components of a received amplitude modulated signal prior to demodulation. The measurement processor also identifies a frequency of a noise component having an amplitude larger than the amplitude of another noise component. A carrier frequency generator generates a carrier frequency substantially at a harmonic of the identified noise component. The carrier frequency is used to generate and demodulate the amplitude modulated signal.

12 Claims, 2 Drawing Sheets

US 7,623,990 B2

SYSTEM FOR REDUCING SIGNAL INTERFERENCE IN MODULATED SIGNAL COMMUNICATION

CROSS-REFERENCED TO RELATED APPLICATION

This is a non-provisional application of U.S. Provisional Application Ser. No. 60/624,670 filed Nov. 3, 2004.

FIELD OF THE INVENTION

The present application relates to a system for reducing signal interference in modulated signal communication, and in particular to a system for improving the performance of a patient medical monitoring system, such as a patient blood oxygen saturation parameter ($SpO_2$) monitoring system, in the presence of signal interference.

BACKGROUND OF THE INVENTION

Patient blood oxygen saturation parameter ($SpO_2$) monitoring systems use light at different wavelengths transmitted through a blood-perfused portion of a patient e.g. a finger or ear lobe, to determine the oxygen saturation parameter of the patient. For example, light emitting diodes (LEDs), emitting light at the desired wavelengths, are arranged to be placed on one side of a patient finger and a photo-detector is arranged to be placed on the other side of the patient finger. The light from the LEDs is transmitted through the finger and detected by the photo-detector. The optical signals from the LEDs are modulated signals at a nominal predetermined carrier frequency. The electrical signal produced by the photo-detector, representing the received optical signal, is demodulated to produce signals representing estimates of the optical signals produced by the LEDs. These signals are processed in a known manner to calculate the oxygen saturation parameter for the patient.

There are several sources of noise interference which are introduced into the system. Electrical noise is introduced into the electrical portion of the $SpO_2$ system by other electrical equipment being operated in the vicinity of the $SpO_2$ system. Optical noise is introduced e.g. by the presence of ambient lighting in the patient room. It is to minimize the adverse affect of such noise that existing systems modulate the signal coupled to the LEDs at the carrier frequency. Subsequent processing involves subtracting adjacent samples, thus minimizing noise and reinforcing desired signals. Typically, however, the largest component of optical noise is introduced by ambient light detected by the photo-detector. Because the ambient light is generated by lights coupled to power mains, it has an AC component at the power mains frequency. This frequency is typically 50 or 60 Hz.

This AC noise component of the optical noise is demodulated. It is possible that harmonics of this interference signal are within the passband of the demodulated received signal and are eliminated or minimized by subtraction. Some existing systems determine a priori expected frequencies of such harmonics, and pre-select a modulation frequency which is expected to minimize the adverse affects of these harmonics. However, such a system having a pre-selected modulation frequency set for one power mains frequency (e.g. 50 Hz) is not be optimum if used with another power mains frequency (e.g. 60 Hz). Other existing systems attempt to detect the presence of such harmonic interference signals in the demodulated signal, and select one of a predetermined set of modulation frequencies which minimizes the adverse affects of the harmonics. This detection process is difficult and complicated, and it is possible that it does not always accurately identify a harmonic frequency. In either case, the frequency of the power mains, while generally at a nominally constant frequency, does vary. Such variation results in degrading the reduction of interference resulting from to the ambient noise.

BRIEF SUMMARY OF THE INVENTION

The inventors realized that if the modulating and demodulating carrier frequency is set to the frequency of a harmonic of the AC interference frequency in the expected passband of the modulated signal, then the harmonics are translated to zero frequency, that is to a DC component signal, in the demodulated signal. In this case, subtraction of a constant from the demodulated signal compensates for the interfering optical signal. To determine the frequencies of the harmonics in the passband, the frequency of the baseband AC interfering signal is determined from the received modulated signal before demodulation. The frequency of a harmonic in the passband of the modulated signal is calculated and the frequency of the carrier signal is locked to that frequency.

In accordance with principles of the present invention, a system for reducing signal interference in modulated signal communication includes a measurement processor. The measurement processor measures amplitudes of noise components of a received amplitude modulated signal prior to demodulation. The measurement processor also identifies a frequency of a noise component having an amplitude larger than the amplitude of another noise component. A carrier frequency generator generates a carrier frequency substantially at a harmonic of the identified noise component. The carrier frequency is used to generate and demodulate the amplitude modulated signal.

DETAILED DESCRIPTION OF THE INVENTION

A processor, as used herein, operates under the control of an executable application to (a) receive information from an input information device, (b) process the information by manipulating, analyzing, modifying, converting and/or transmitting the information, and/or (c) route the information to an output information device. For example, it is possible for a processor to comprise the capabilities of a controller or microprocessor. It is further possible for the processor to operate with a display processor or generator. A display processor or generator is a known element for generating signals representing display images or portions thereof. A processor and a display processor comprises any combination of, hardware, firmware, and/or software.

An executable application, as used herein, comprises code or machine readable instructions for conditioning the processor to implement predetermined functions, such as those of an operating system, patient medical monitoring system such as a patient blood oxygen saturation parameter ($SpO_2$) monitoring system, or other information processing system, for example, in response to user command or input. An executable procedure is a segment of code or machine readable instruction, sub-routine, or other distinct section of code or portion of an executable application for performing one or more particular processes. These processes include, among other things, receiving input data and/or parameters, performing operations on received input data and/or performing functions in response to received input parameters, and providing resulting output data and/or parameters.

Figure 1:
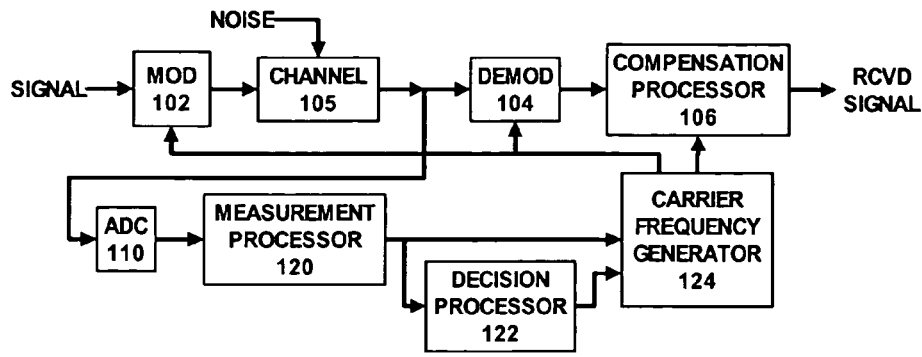
FIG. 1 is a block diagram of a system for reducing signal interference in modulated signal communication according to principles of the present invention.

FIG. 1 is a block diagram of a system for reducing signal interference in modulated signal communication according to principles of the present invention. In FIG. 1, a signal input terminal is coupled to a source (not shown) of a signal to be transmitted. The signal input terminal is coupled to a signal input terminal of a modulator 102. An output terminal of the modulator 102 generates a modulated signal which is supplied to a communication channel 105. A signal input terminal of a demodulator 104 is coupled to receive a signal from the channel 105. An output terminal of the demodulator 104 is coupled to a signal input terminal of a compensation processor 106. An output terminal of the compensation processor 106 is coupled to an output terminal producing a processed received signal. The output terminal is coupled to a signal processing unit (not shown) which processes the received signal.

An input terminal of an analog-to-digital converter (ADC) 110 is also coupled to receive the signal from the channel 105. An output terminal of the ADC 110 is coupled to a measurement processor 120. An output terminal of the measurement processor 120 is coupled to an input terminal of a decision processor 122, and a first input terminal of a carrier frequency generator 124. An output terminal of the decision processor 122 is coupled to a second input terminal of the carrier frequency generator 124. A carrier signal output terminal of the carrier frequency generator 124 is coupled to respective carrier input terminals of the modulator 102 and the demodulator 104. A control output terminal of the carrier frequency generator 124 is coupled to a control input terminal of the compensation processor 106.

In operation, the modulator 102 amplitude modulates a signal on a carrier signal supplied to the modulator 102 by the carrier frequency generator 124. The modulated signal is transmitted through the channel 105 to the demodulator 104. One or more noise components are introduced into the transmitted amplitude modulated signal in the channel 105, as described above. The demodulator 104 demodulates the received amplitude modulated signal, using the carrier signal supplied by the carrier frequency generator 124 as a local oscillator signal, to detect the signal modulated on the carrier.

The ADC 110 performs analog-to-digital conversion of the received signal, generating digital samples representing the received amplitude modulated signal, including the signal component and the noise components, prior to demodulation by the demodulator 104. The measurement processor 120 measures noise components by measuring at least one of: (a) amplitude, (b) frequency, (c) harmonic content, and (d) waveform morphology of the received amplitude modulated signal prior to demodulation. The frequency of a noise component having an amplitude larger than the amplitude of another noise component is identified. More specifically, in the illustrated embodiment, the frequency of a noise component having an amplitude larger than the respective amplitudes of the remaining noise components is identified. That is, the identified noise component frequency is the frequency of the noise component having: (a) substantially the largest amplitude noise component in the received amplitude modulated signal, and/or (b) substantially the largest, or equally largest, amplitude noise component in the received amplitude modulated signal.

The measurement processor 120 supplies data representing the noise component frequency identified as having the largest amplitude to the carrier frequency generator 124. The carrier frequency generator 124 generates a carrier signal substantially at a harmonic of the noise component identified by the measurement processor 120. This carrier signal is used by the modulator 102 and demodulator 104 in generating and demodulating the amplitude modulated signal. The measurement processor 120 and carrier frequency generator 124 operate continually, allowing the frequency of the carrier signal to track the identified frequency of the noise component having the largest amplitude.

It is expected that the frequency of the noise component having the largest amplitude is the frequency of the ambient light, i.e. the AC mains frequency (e.g. 50 Hz or 60 Hz). For example, the measurement processor 120 operates to identify 60 Hz as the frequency of the noise component having the largest amplitude, to condition the carrier frequency generator 124 to generate a carrier signal at a harmonic of the 60 Hz AC mains frequency, and to track variations in that frequency. If the expected passband of the amplitude modulated signal is from 500 Hz to 700 Hz, then the $9^{th}$, $10^{th}$, and $11^{th}$ harmonics of 60 Hz: i.e. 540 Hz, 600 Hz, and 660 Hz, lie within the passband. In this case, the measurement processor 120 conditions the carrier frequency generator 124 to generate a carrier frequency at one of the harmonics, e.g. the $10^{th}$ harmonic, or 600 Hz. Because the carrier frequency is set to and tracks one of these harmonics, e.g. the $10^{th}$ harmonic, 600 Hz, the frequency of these harmonics after demodulation by the demodulator 104 is 0 Hz. This results in a DC component being associated with that noise component in the demodulated signal from the demodulator 104. The carrier frequency generator 124 supplies data representing the expected DC component to the compensation processor 106, which subtracts the expected DC component associated with that noise component from the demodulated signal, thereby minimizing the noise component having the largest amplitude.

The measurement processor 120 typically identifies the frequency of the AC mains as the noise component having the largest amplitude. However, it is possible that a different noise component, having a different fundamental frequency, has the largest amplitude. For example, electro-cautery equipment in operating rooms generate relatively large amounts of electronic interference, possibly having a larger amplitude than the optical interference from ambient lighting. The combination of the measurement processor 120 and carrier frequency generator 124 identifies the frequency of this noise component and generate a carrier signal which tracks the frequency of harmonics of this noise component within the passband of the demodulated signal.

It is possible for the carrier frequency to be determined in the following manner. The received modulated signal is filtered before demodulation to minimize the desired signal information representing the optical signals from the LEDs, and to pass primarily the noise components. The fundamental noise frequency is measured by any known means, such as use of a fast Fourier transform (FFT), or counting the number of clock cycles between two or more zero crossings of the filtered signal. Alternatively, if no optical signal from the LEDs is produced, the interfering noise components is able to be measured without requiring filtering of the signal information produced by the LEDs. In either case, the nominal carrier frequency is divided by the fundamental noise frequency and the result rounded to the nearest integer to determine the noise component harmonic to which the carrier frequency is locked. Following the example above, if the desired passband is from 500 Hz to 700 Hz, the nominal carrier frequency is 600 Hz. The AC mains frequency is 60 Hz. The quotient of 600 divided by 60 is 10. Thus, the $10^{th}$ harmonic is selected to be the carrier frequency. A carrier frequency which tracks the $10^{th}$ harmonic of the AC mains frequency (e.g. nominally 600 Hz) is generated and used in generating and demodulating the amplitude modulated signal. This results in the noise component being transformed to DC when demodulated as described above.

Also as described above, the identification of the frequency of the noise component having the largest amplitude is done continually. The update rate depends on the characteristics of the noise component and the desired performance of the system.

While typically, it is expected that a single noise component has the largest amplitude, it is possible for the measurement processor 120 to detect multiple noise components having substantially equal amplitudes larger than another noise component, or having the largest or equally largest amplitudes. In such a case, it is not possible to identify a frequency of a noise component having the largest amplitude. In response to identifying multiple noise components of substantially equal amplitude, the decision processor 122 inhibits the carrier frequency generator 124 from generating a carrier frequency substantially at a harmonic of an identified noise component. In this case the carrier frequency generator 124 is conditioned to generate a carrier signal at a nominal frequency (continuing the above example, at 600 Hz). Alternatively the carrier frequency generator uses one of a plurality of known techniques, used by existing systems, to select a carrier frequency.

Figure 2:
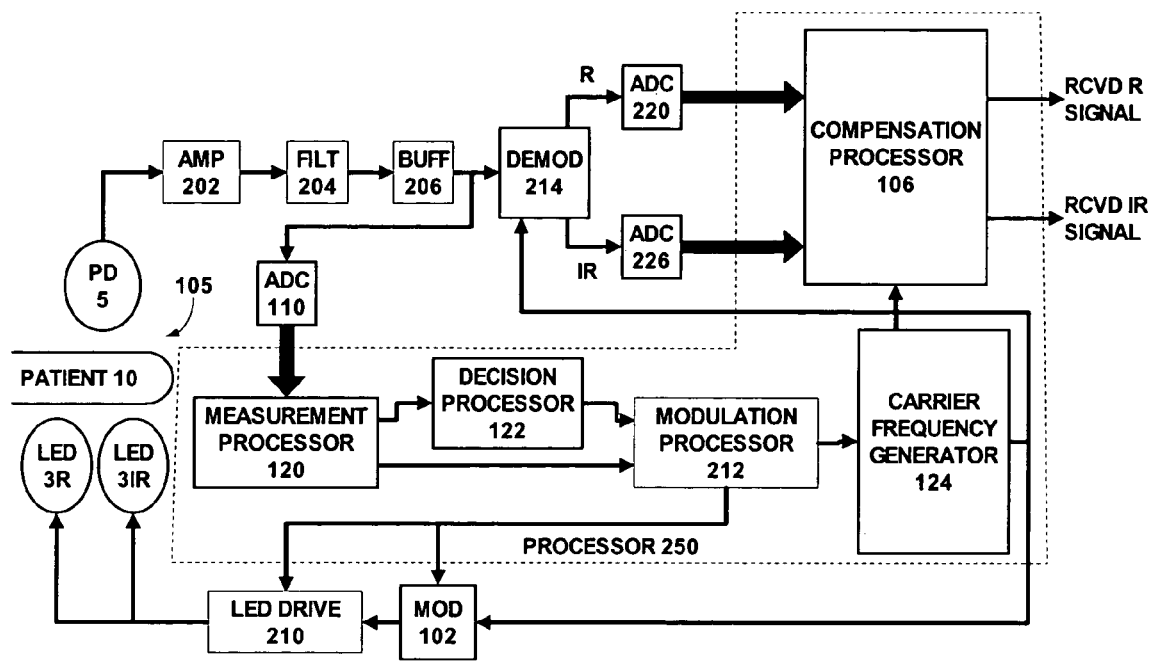
FIG. 2 is a more detailed block diagram of the system illustrated in FIG. 1 according to principles of the present invention.

A system such as that described above is used in a patient medical parameter monitoring system, such as a patient blood oxygen saturation parameter ($SpO_2$) monitoring system. FIG. 2 is a more detailed block diagram of the system illustrated in FIG. 1 according to principles of the present invention as embodied in an $SpO_2$ monitoring system. In FIG. 2, elements which are the same as those illustrated in FIG. 1 are designated by the same reference number and are not described in detail below.

In FIG. 2, an output terminal of a modulator 102 is coupled to an input terminal of an light-emitting-diode (LED) drive circuit 210. An output terminal of the LED drive circuit 210 is coupled to respective terminals of LED 3R and LED 3IR. LED 3R emits red light when activated and LED 3IR emits infrared (IR) light when activated. A photo-detector 5 is arranged to receive light signals from the LEDs 3R and 3IR. A blood-perfused portion of a patient 10, for example, a finger or ear lobe, is placed between the LEDs 3R and 3IR and the photo-detector sensor 5. This operates as the channel 105. The light generated by the LEDs 3R and 3IR is detected by the photo-detector device 5 following transmission through patient blood and tissue 10. An output terminal of the photo-detector sensor 5 is coupled to a series connection of an amplifier 202, a filter 204 and a buffer amplifier 206. An output terminal of the buffer amplifier 206 is coupled to a signal input terminal of a demodulator 214 and an input terminal of an ADC 110. A first output terminal of the demodulator 214 generates a signal representing the signal from the LED 3R and is coupled to a second ADC 220. A second output terminal of the demodulator 214 generates a signal representing the signal from LED 3IR and is coupled to a third ADC 226. The respective output terminals of the ADC 220 and ADC 226 are coupled to corresponding input terminals of a compensation processor 106. An output terminal of the compensation processor generates a processed received signal.

An output terminal of the ADC 110 is coupled to an input terminal of a measurement processor 120. An output terminal of the measurement processor 120 is coupled to respective input terminals of a decision processor 122 and a modulation processor 212. An output terminal of the modulation processor 212 is coupled to an input terminal of a carrier frequency generator 124. A carrier signal output terminal of the carrier frequency generator 124 is coupled to respective input terminals of the modulator 102 and the demodulator 214, and a control output terminal of the carrier frequency generator 124 is coupled to a control input terminal of the compensation processor 106. A control output terminal of the modulation processor 212 is coupled to respective control input terminals of the LED drive circuit 210 and the modulator 102.

In operation, the modulator 102 modulates the carrier frequency from the carrier frequency generator 124 at the frequency of the noise component having the largest amplitude for transmission by the LEDs 3R and 3IR, as described above. The modulator 102 conditions the LED drive circuit 210 to drive the LEDs 3R and 3IR so as to produce an optical signal corresponding to the modulated carrier signal. The photo-detector sensor 5 detects an optical signal and provides an output voltage signal having a signal component representing the light generated by the LEDs 3R and 3IR and one or more noise components. The photo-detector sensor 5 output voltage signal is amplified by amplifier 202, filtered by filter 204 and buffered by buffer amplifier 206. One skilled in the art understands that it is possible to apply any or all of these signal processing functions and/or other similar signal processing functions to the photo-detector 5 output voltage signal to provide a signal having characteristics which are more easily processed by subsequent circuitry. One use for such processing is to reduce noise components which are more easily reduced before subsequent processing. For example, high frequency out-of-band noise is reduced by low-pass filtering.

The demodulator 214 demodulates the signal modulated on the noise component harmonic carrier frequency, received by the photo-detector sensor 5 and transmitted using the LEDs 3R and 3IR, to provide respective demodulated red and IR signals. These signals are converted to digital samples by the respective ADCs 220 and 226. The compensation processor 106 operates in a first mode of operation on the signal representing the optical signal transmitted by the red LED 3R and in a second mode of operation on the signal representing the optical signal transmitted by the IR LED 3IR. It is possible for the noise representative DC component for the signal representing the red LED 3R to be the same as or different from the noise representative DC component for the signal representing the IR LED 3IR. In the first and second operating modes, the compensation processor 106 operates to process the respective demodulated signals by subtracting the appropriate DC component, associated with the noise component having the largest amplitude, from the corresponding demodulated LED signal (3R or 3IR). The compensation processor 6, thus, generates respective red and IR received signals in which that noise component is minimized. These signals are further processed in a known manner to calculate, display, record and/or transmit to another location the $SpO_2$ parameter.

The measurement processor 120 measures the amplitudes of the noise components of the received amplitude modulated signal prior to demodulation, and identifies the frequency of the noise component having an amplitude larger than another noise component, for example, the noise component having the largest amplitude. The identified frequency of this noise component is supplied to the modulation processor 212. The modulation processor 212 adjusts at least one of: (a) the modulation frequency, (b) the modulation drive pattern, and (c) type of modulation of the LEDs 3R and 3IR. More specifically, in the illustrated embodiment, the modulation processor 212 conditions the carrier frequency generator 124 to generate a carrier frequency signal for the LEDs 3R and 3IR substantially at a harmonic of the identified noise component signal. The generated carrier frequency signal substantially at the harmonic of the identified noise component is employed in generating and demodulating the amplitude modulated signal.

As described above, it is possible for the measurement processor 120 to measure the noise component more accurately by transmitting an unmodulated signal and measuring the noise components of the received unmodulated signal before demodulation. The LED drive circuit 210 is able to (a) change the amplitude of LED drive power, and/or (b) reduce to zero LED drive power, during the process of identifying and measuring noise components. The modulation processor 212 is able to condition the modulator 102 to employ one of a plurality of LED modulation drive patterns and/or to adjust the type of modulation provided to the LEDs 3R and 3IR. In addition, the modulation processor 212 is able to condition the LED drive circuit 210 to reduce the LED drive to zero to enable the measurement processor 120 to measure the noise components with no signal component present.

Also a described above, it is possible that multiple noise components have substantially equal amplitudes. In this case, the decision processor 122 inhibits the modulation processor 212 from conditioning the carrier frequency generator 124 to generate a carrier frequency substantially at a harmonic of an identified noise component. Instead, the modulation processor 212 is able to set the carrier frequency by one of the plurality of known methods, as described above. The modulation processor 212 is also able to control the amplitude of LED drive power, and the modulation drive pattern and type of modulation, for the LEDs 3R and 3IR when responding to the condition of having multiple noise components having substantially equal amplitudes.

The compensation processor 106, measurement processor 120, decision processor 122, modulation processor 212 and carrier frequency generator 124 are illustrated as being embodied in a processor 250. In FIG. 2, the processor 250 has respective digital input terminals for receiving digital samples representing the demodulated red LED 3R representative signal, the demodulated IR LED 3IR representative signal and the signal representing the optical signal prior to demodulation. The processor 250 also has respective control output terminals for controlling the carrier frequency signal used by the modulator 102 and demodulator 214, the LED drive power generated by the LED drive circuit 210, and the modulation drive pattern and type of modulation produced by the modulator 102. The processor 250 also is illustrated as having respective output terminals producing noise reduced received red and IR representative signals. One skilled in the art understands the processor 250 is able to implement other functions. Among those other functions is processing the noise reduced red and IR signals to calculate, store, and/or transmit to another location, the SpO$_2$ parameter. It is further possible that the processor 250 cooperates with a display processor (not shown) to generate an image displaying the SpO$_2$ parameter for clinicians. These other functions are not germane to the present invention, and are not described in detail.

Figure 3:
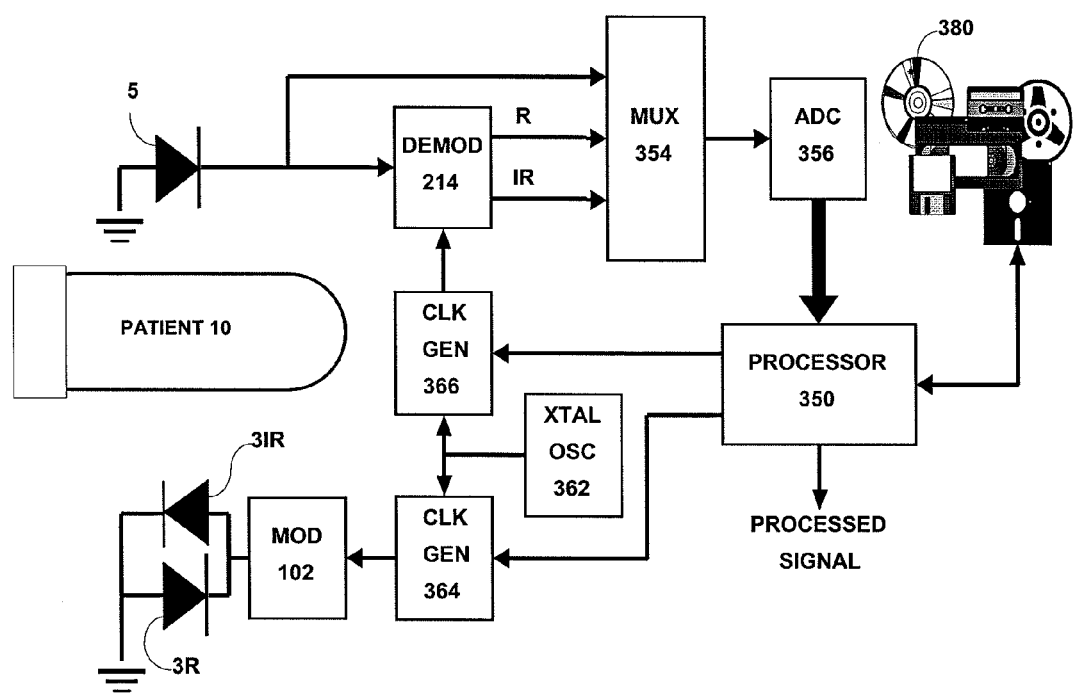
FIG. 3 is a more detailed block diagram of another embodiment of the system illustrated in FIG. 1 according to principles of the present invention.

FIG. 3 is a more detailed block diagram of another embodiment of the system illustrated in FIG. 1 according to principles of the present invention. In FIG. 3, elements which are the same as those illustrated in FIG. 1 and FIG. 2 are designated by the same reference number and are not described in detail below. In FIG. 3, an output terminal of a crystal oscillator 362 is coupled to respective input terminals of a first clock generator 364 and a second clock generator 366. An output terminal of the first clock generator 364 is coupled to the modulator 102 and an output terminal of the second clock generator 366 is coupled to an input terminal of the demodulator 214. The modulator 102 is coupled to a parallel connection of a red LED 3R and an IR LED 3IR. The photo-detector sensor 5 is illustrated as a photodiode. An output terminal of the photodiode 5 is coupled to a first input terminal of a multiplexer 354 and an input terminal of the demodulator 214. Respective first and second output terminals of the demodulator 214 are coupled to corresponding input terminals of the multiplexer 354. An output terminal of the multiplexer 354 is coupled to an input terminal of an ADC 356. An output terminal of the ADC 356 is coupled to an input terminal of the processor 350.

The processor has first and second control output terminals respectively coupled to the first clock generator 364 and the second clock generator 366. The processor 350 also has an output terminal for producing the noise reduced processed signal, either respective red and IR light representative signals, or a signal representing the SpO$_2$ parameter, or a signal representing an image displaying the SpO$_2$ parameter for reproduction on a display device (not shown). The processor 350 also includes a bidirectional terminal coupled to tangible storage media 380.

In operation, the combination of the crystal oscillator 362 and the clock generator 364 produces a carrier signal for the modulator 102. For example, the crystal oscillator 362 is able to generate a relatively high frequency oscillatory signal. In one embodiment, the clock generator 364 includes a relatively high resolution controllable divider, controlled by a signal from the processor 350. The clock generator 364 is controlled by a signal produced by the executable application or executable procedure implementing the portion of the carrier frequency generator 124 which controls the frequency of the carrier frequency signal. This signal conditions the clock generator 364 to set a divide factor which divides the relatively high frequency signal from the crystal oscillator 362 by the appropriate amount to produce a carrier signal at the desired frequency. The combination of the crystal oscillator 362 and the clock generator 366 operates in the same manner to produce a carrier signal for the demodulator 214, and is typically controlled to produce a clock signal at the same frequency as the clock signal generated by the clock generator 364 for the modulator 102.

The red LED 3R is coupled in parallel with, but opposed to, the IR LED 3IR. In response to positive cycles of the modulation signal from the modulator 102, the IR LED 3IR produces an optical signal, and in response to negative cycles of the modulation signal from the modulator 102, the red LED 3R produces an optical signal. As described above, these optical signals are transmitted through patient blood and tissue 10 and are detected by the photodiode 5. The ADC 356 is a relatively high speed ADC which is capable of performing the analog-to-digital conversion of the received signal from the photodiode 5, the received red LED 3R signal, and the received IR LED 3IR signal. The multiplexer 354 couples a signal at one of the input terminals to the ADC 356 at a time and the ACD 356 produces a digital sample representing that signal.

The processor 350 includes an executable application, and possibly respective executable procedures, which perform the functions of the measurement processor 120, the decision processor 122, the modulation processor 212, the compensation processor 106 and at least a portion of the carrier frequency generator, i.e. the portion of the carrier frequency generator 124 which controls the frequency of the carrier frequency signal generated (FIG. 1 and FIG. 2). As the processor 350 receives digital samples from the ADC 356, they are routed to the appropriate executable procedure. For example, samples representing the signal from the photodiode 5 before demodulation are routed to the executable procedure implementing the operations of the measurement processor 120. Samples representing the received demodulated red and IR LED (3R, 3IR) signals are routed to the executable procedure implementing the operations of the compensation processor 106. Similarly, the executable procedures condition the processor 350 to generate appropriate control signals. For example, the executable procedure implementing the portion of the carrier frequency generator 124 which controls the frequency of the carrier frequency signal generated conditions the processor 350 to produce the control signal supplied to the first and second clock signal generators 364 and 366. These signals condition the first and second clock signal generators 364 and 366 to produce respective carrier signals at the desired frequency as described above.

The processor 350 is bidirectionally coupled to the tangible storage media 380. The tangible electronic data storage media 380 includes magnetic devices such as reel-to-reel computer tape, cassette tapes, and magnetic disk media such as floppy disks, and so forth. The tangible electronic data storage media 380 also includes optical devices, such as digital video disks (DVD) or compact disks (CD) and so forth. The tangible electronic data storage media 380 also includes portable storage devices such as semiconductor memory integrated circuits and so forth. The tangible storage media 380 is capable of storing any data. More specifically, in the illustrated embodiment, the machine readable instructions forming the executable application and/or executable procedures for performing the activities in the system described above are stored in a tangible storage medium 380. The processor 350 retrieves the machine readable instructions for performing the activities of the executable application and/or executable procedures from the appropriate tangible electronic data storage medium 380, and stores them in the memory (not shown) included in the processor 350. The processor 350 then executes the executable application and/or executable procedures stored in the memory to perform the activities described above.

The system is illustrated in FIG. 3 to include only those elements necessary to understand the operation of such a system using a processor executing an executable application and respective executable procedures to perform the activities of elements illustrated in FIG. 1 and FIG. 2. One skilled in the art understands that the processor 350 includes executable procedures to implement other functions, e.g. to calculate the value of the SpO$_2$ parameter and generate image representative signals for conditioning a display device to display the SpO$_2$ parameter. It is also possible for the system illustrated in FIG. 3 to include other circuitry illustrated in FIG. 2, including the LED drive circuit 210, amplifier 202, filter 204, and buffer amplifier 206.

One skilled in the art understands that it is possible to modulate the red LED 3R and IR LED 3IR at different modulation frequencies in order to reject different noise components for the red and IR optical channels, respectively. One skilled in the art also understands that the processing functions described above with respect to FIG. 1, FIG. 2 and/or FIG. 3 are able to be performed in hardware, software or a combination of both.

What is claimed is:

1. A system for reducing signal interference in modulated signal communication, comprising:
    a measurement processor for,
        measuring amplitudes of noise components of a received amplitude modulated signal prior to demodulation,
        identifying a frequency of a noise component having an amplitude larger than the amplitude of another noise component; and
    a carrier frequency generator for generating a carrier frequency at a harmonic of said identified noise component for use in generating and demodulating said amplitude modulated signal; and
    a demodulator for demodulating a received signal modulated at said noise component harmonic carrier frequency to provide a demodulated signal; and
    a compensation processor for processing said demodulated signal and subtracting a DC component associated with said noise component from said processed demodulated signal.

2. The system of claim 1 further comprising an analog-to-digital converter (ADC) for analog-to-digital conversion of said received signal modulated at said noise component harmonic carrier frequency prior to demodulation.

3. A system for reducing signal interference in modulated signal communication, comprising:
    a measurement processor for,
        measuring amplitudes of noise components of a received amplitude modulated signal prior to demodulation,
        identifying a frequency of a noise component having an amplitude larger than the amplitude of another noise component;
    a carrier frequency generator for generating a carrier frequency at a harmonic of said identified noise component for use in generating and demodulating said amplitude modulated signal, wherein said measurement processor identifies multiple noise components of equal amplitude, said equal amplitude being larger than another noise component, and
    a decision processor for inhibiting said carrier frequency generator from generating a carrier frequency at said harmonic of said identified noise component, in response to said identification of multiple noise components of equal amplitude.

4. A system for reducing signal interference in modulated signal communication, comprising:
    a measurement processor for,
        measuring amplitudes of noise components of a received amplitude modulated signal prior to demodulation,
        identifying a frequency of a noise component having an amplitude larger than the amplitude of another noise component; and
    a carrier frequency generator for generating a carrier frequency at a harmonic of said identified noise component for use in generating and demodulating said amplitude modulated signal; wherein:
    a light emitting diode (LED);
    a photo-detector sensor for providing an output voltage signal in response to light generated by said LED;
    a modulator for modulating a carrier frequency at said noise component harmonic for transmission using said LED; and
    a demodulator for demodulating a signal modulated on said noise component harmonic carrier frequency received by said photo-detector sensor and transmitted using said LED, to provide a demodulated signal.

5. The system of claim 4 further comprising an LED drive unit for at least one of: (a) changing the amplitude of LED drive power, and (b) reducing to zero LED drive power, during identifying and measuring noise components.

6. The system of claim 4 further comprising a modulation processor that adjusts at least one of: (a) modulation frequency, (b) modulation drive pattern, and (c) type of modulation of said LED.

7. The system of claim 4 further comprising a modulation processor that adjusts LED modulation frequency to substantially match the frequency of a harmonic of the identified noise component signal.

8. The system of claim 4 further comprising a compensation processor for processing said demodulated signal and subtracting a DC component associated with said noise component from said processed demodulated signal.

9. The system of claim 4 wherein said sensor output voltage signal is provided by at least one of: (a) amplification, (b) filtering, and (c) buffering of a signal provided by a photo-detector device.

10. The system of claim 4 wherein said system is for patient blood oxygen saturation parameter monitoring.

11. The system of claim 4 wherein said light generated by said LED is detected by said photo-detector device following transmission through patient blood and tissue.

12. The system of claim 4 wherein said LED comprises a red and an infra-red LED and said system performs measurements and compensation of sensor output voltage in a first mode in response to light provided by said red LED and in a second mode in response to light provided by said infra-red LED.

* * * * *